United States Patent [19]

Rodriguez et al.

[11] Patent Number: 5,220,061
[45] Date of Patent: Jun. 15, 1993

[54] SELECTIVE PROCESS FOR THE PREPARATION OF DIPHENYLMETHANE BIS-(DIALKYL UREAS

[75] Inventors: Carmen L. Rodriguez, Exton; Edward T. Shawl, Wallingford; Haven S. Kesling, Jr., Drexel Hill, all of Pa.

[73] Assignee: Arco Chemical Technology, L.P., Wilmington, Del.

[21] Appl. No.: 963,167

[22] Filed: Oct. 19, 1992

Related U.S. Application Data

[62] Division of Ser. No. 832,251, Feb. 7, 1992.

[51] Int. Cl.$^5$ .............................................. C07C 273/18
[52] U.S. Cl. ................................... 564/50; 564/55
[58] Field of Search .................................. 564/55, 50

[56] References Cited

U.S. PATENT DOCUMENTS

| | | | |
|---|---|---|---|
| 4,422,871 | 12/1988 | Schirmer et al. | 564/55 |
| 4,820,871 | 4/1989 | Kissener et al. | 564/50 |
| 4,996,359 | 2/1991 | Kesling, Jr. et al. | 564/50 |

FOREIGN PATENT DOCUMENTS 0756638  4/1967  Canada ............................. 260/554

Primary Examiner—José G. Dees
Assistant Examiner—Samuel Barts
Attorney, Agent, or Firm—Jonathan L. Schuchardt

[57] ABSTRACT

A selective process for the preparation of diphenylmethane bis(dialkylureas) is disclosed. An alkyl phenylcarbamate or an N,N-dialkyl-N'-phenylurea is reacted with a methylene bis(alkyl carbamate) in the presence of an acid catalyst. The use of a staged addition of phenylcarbamate or phenylurea to the methylene bis(carbamate) and the use of a ramped temperature program are the keys to good selectivity to MDI dimer products.

8 Claims, No Drawings

SELECTIVE PROCESS FOR THE PREPARATION OF DIPHENYLMETHANE BIS-(DIALKYL UREAS)

This is a division of application Ser. No. 07/832,251, filed Feb. 7, 1992, now allowed.

FIELD OF THE INVENTION

The invention relates to the synthesis of diphenylmethane diisocyanate (MDI) precursors. The precursors are dicarbamates and bis(dialkylureas) of diphenylmethane, which can be cracked thermally with or without a reaction promoter to give diisocyanates. The diisocyanates are useful for the manufacture of polyurethanes.

BACKGROUND OF THE INVENTION

Diphenylmethane dicarbamates and diphenylmethane bis(dialkylureas) are useful precursors to diphenylmethane diisocyanates. Either the dicarbamates (U.S. Pat. No. 3,962,302) or the bis(dialkylureas) (U.S. Pat. Nos. 3,936,484, 4,871,871, 4,873,364) decompose thermally and/or in the presence of a promoter to give the diisocyanates.

Conventional approaches to diphenylmethane dicarbamates focus on the condensation of an alkyl phenylcarbamate with formaldehyde or its equivalent in the presence of an acid catalyst. This approach is illustrated in U.S. Pat. Nos. 2,946,768, 4,162,362, 4,202,986, 4,287,132, 4,543,419, and in Japanese Kokai Nos. 2--83363 and 2-3658. Unfortunately, the reaction of alkyl phenylcarbamates with formaldehyde under acid conditions is complicated by side reactions. Formaldehyde reacts at the carbamate nitrogen to give undesirable N-(alkoxycarbonyl)phenylaminomethylphenyl compounds, or so-called "N-benzyl compounds," which include dimers, trimers, tetramers, etc. of these compounds. Polycondensation products—polymethylene polyphenylene dicarbamates—also form, and the formation of such polynuclear compounds is difficult to suppress. Consequently, it is difficult to selectively prepare diphenylmethane dicarbamates. Unlike TDI-like diisocyanates, diphenylmethane diisocyanates are not easily purified by distillation, so techniques such as fractional crystallization must be used to purify the diisocyanates or precursors. This fact makes good control over product selectivity especially critical. A preferred process is one that minimizes or eliminates polycondensation and other side products.

As an alternative to formaldehyde, alkylmethylene bis(alkyl carbamates) have been used as alkylating agents. Japanese Patent No. 63-203655 (1988) describes the preparation of-p-loymethylene polyphenylene dicarbamates from the reaction of benzene and an alkylmethylene bis(alkyl carbamate). Murphy and Raman (J. Chem. Soc., Perkin Trans. I (1981) 447) show that ethyl phenylcarbamate reacts with methylene bis(ethyl carbamate) in the presence of boron trifluoride etherate to give a mixture of 4-(N-ethoxycarbonylaminoethyl)-N-ethoxycarbonylaniline (II) and diphenylmethane-4,4,-bis(ethyl carbamate) (III):

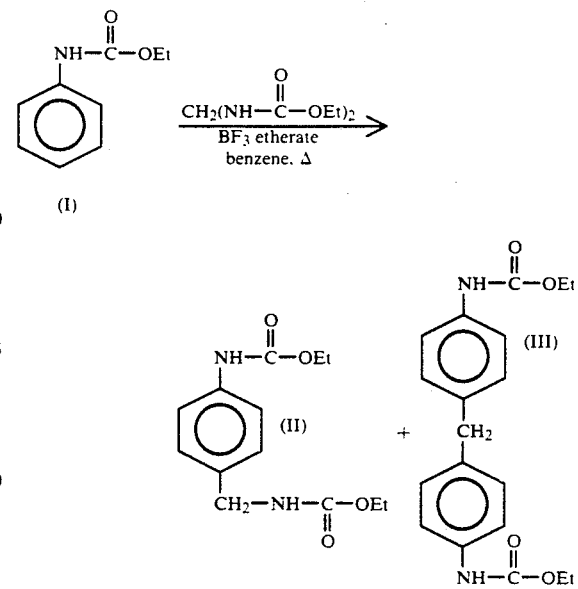

Reaction in refluxing benzene over 24 hours gives 43% conversion of (I), with 77% selectivity to the intermediate product 23% selectivity to the MDI dimer precursor (III). Although the desired MDI dimer precursors are obtained, conversion and selectivity are lower than desirable for commercial use.

A process for making diphenylmethane diisocyanate precursors with high conversion, relatively short reaction time, and high selectivity to dimer products is needed. Preferably, the conversion of the intermediate products is complete, and formation of undesirable N-benzyl compounds or polymethylene polyphenylene diisocyanate precursors is minimized or avoided.

SUMMARY OF THE INVENTION

The invention is a process for making diphenylmethane diisocyanate precursors. The precursors, which are dicarbamates or bis(dialkylureas) of diphenylmethane, are obtained in high yields with good selectivity to dimer products.

One process of the invention, which is a process producing a diphenylmethane dicarbamate, comprises: (a) slowly adding a mixture of an alkyl phenylcarbamate and an effective amount of an acid to a methylene bis(alkyl carbamate) at a temperature within the range of about 20° C. to about 55° C. to produce an aryl-alkyl dicarbamate; and (b) heating the aryl-alkyl dicarbamate in the presence of additional alky phenylcarbamate at a temperature within the range of about 60° C. to about 100° C. for a time sufficient to produce the diphenylmethane dicarbamate.

In another process of the invention, a diphenylmethane bis(dialkylurea) is produced. In this process, an N,N-dialkyl-N'-phenylurea is used in place of the alkyl phenylcarbamate. The intermediate product is an aryl urea-alkyl carbamate, which is heated in the presence of additional N,N-dialkyl-N'-phenylurea to produce a diphenylmethane bis(dialkylurea).

DETAILED DESCRIPTION OF THE INVENTION

The diphenylmethane diisocyanate precursors made by the process of the invention are dicarbamates or bis(dialkylureas) of diphenylmethane. The dicarbamates are made using an alkyl phenylcarbamate, while the bis(dialkylureas) are prepared from N,N-dialkyl-N'-phenylureas.

Alkyl phenylcarbamates useful in the process of the invention preferably have the general formula Ph-NH-CO-OR in which R is a linear, branched, or cyclic $C_1$-$C_{20}$ alkyl, aryl, or aralkyl group. Suitable alkyl phenylcarbamates include, but are not limited to, methyl phenylcarbamate, ethyl phenylcarbamate, n-butyl phenylcarbamate, benzyl phenylcarbamate, diphenylcarbamate, and the like, and mixtures thereof.

N,N-Dialkyl-N'-phenylureas useful in the process of the invention have the general formula Ph-NH-CO-NR'R" in which each of R' and R" separately represents a linear, branched, or cyclic $C_1$-$C_{20}$ alkyl group. Suitable N,N-dialkyl-N'-phenylureas include, but are not limited to, N,N-dimethyl-N,-phenylurea, N,N-diethyl-N'-phenylurea, N,N-dibutyl-N,-phenylurea, and the like, and mixtures thereof.

In the process of the invention, the alkyl phenylcarbamate or N,N-dialkyl-N'-phenylurea reacts with a methylene bis(alkyl carbamate). The methylene bis(alkyl carbamate) preferably has the general structure R"RC(NH—CO—OR")$_2$ in which each of R and R' separately represents hydrogen or a linear, branched, or cyclic $C_1$-$C_{30}$ alkyl, aryl, or aralkyl group; and R" represents a linear, branched, or cyclic $C_1$-$C_{20}$ alkyl, aryl, or aralkyl group. Preferably, R and R' are both hydrogen, and R" is methyl or ethyl. Suitable methylene bis(alkyl carbamates) include, but are not limited to, methylene bis(methyl carbamate), methylene bis(ethyl carbamate), dimethylmethylene bis(ethyl carbamate), and the like, and mixtures thereof. A methylene bis(dialkylurea), such as methylene bis(diethylurea), methylene bis(dimethylurea), or the like, may be used in place of the methylene bis(alkyl carbamate). For example, ethyl phenylcarbamate reacts with an equivalent of methylene bis(diethylurea) to give intermediate product (IV). Reaction of (IV) with another equivalent of ethyl phenylcarbamate gives the desired diphenylmethane dicarbamate:

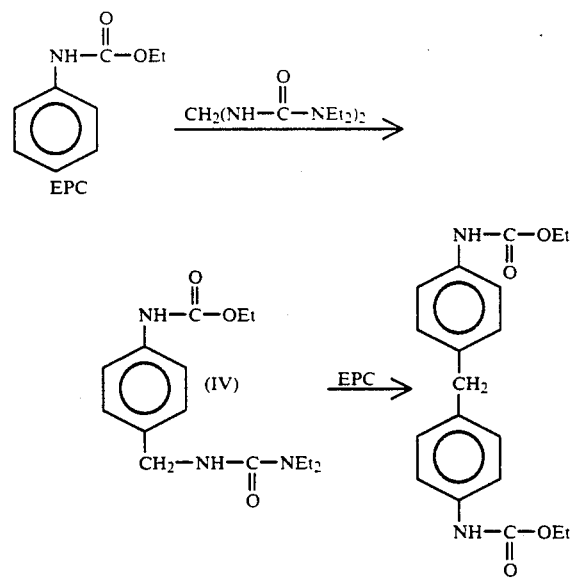

An acid catalyst is used in the process of the invention. The acid may be a protic acid or a Lewis acid. Preferred acids are protic acids that have a $pK_a$ less than about 0. Suitable acids include, but are not limited to, hydrochloric acid, sulfuric acid, trifluoromethanesulfonic acid, trichloroacetic acid, phosphotungstic acid, antimony pentachloride, chlorosulfonic acid, fluorosulfonic acid, fluoroboric acid, trifluoroacetic acid, and the like, and mixtures thereof.

Although any desired amount of acid can be used, it is preferred to use an amount within the range of about 0.01 to about 1.0 equivalents of acid per equivalent of alkyl phenylcarbamate or N,N-dialkyl-N'-phenylurea. A more preferred range is from about 0.05 to about 0.15 equivalents.

The desired products from the process of the invention are diphenylmethane dicarbamates or diphenylmethane bis(dialkylureas). The reaction of ethyl phenylcarbamate with methylene bis(methylcarbamate), for example, gives diphenylmethane 2,4'- and 4,4'-dicarbamates (V) as the desired products:

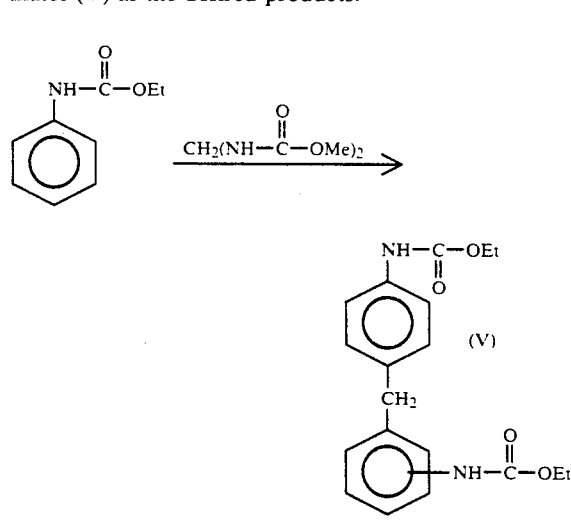

Other observed products include the intermediate arylalkyl dicarbamate (VI) and polycondensation products:

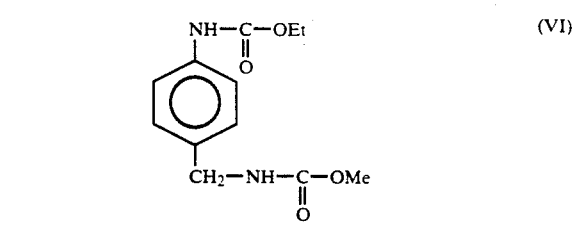

The key to the invention is the discovery that selectivity to the desired products (e.g., (V)) is substantially improved by (a) utilizing a staged addition of alkyl phenylcarbamate or N,N-dialkyl-N'-phenylurea to the reaction mixture, and (b) using a ramped reaction temperature program characterized by a relatively low-temperature first stage and a relatively high-temperature second stage.

Staged addition of alkyl phenylcarbamate or N,N-dialkyl-N'-phenylurea is important. In the first stage, the phenylcarbamate or phenylurea is added (optionally as a solution in an organic solvent) slowly to an approximately equivalent amount of a methylene bis(alkyl carbamate), and is allowed to react in the presence of an acid catalyst until an intermediate product such as (VI)

forms. It is preferred to use a molar ratio of phenylcarbamate or phenylurea to methylene bis(alkyl carbamate) within the range of about 0.8 to about 8. A more preferred range is from about 0.8 to about 1.5. Most preferred is the range from about 0.9 to about 1.1. The acid catalyst is preferably combined with the phenylcarbamate or phenylurea before adding to the methylene bis(alkyl carbamate). In the second stage of the addition, a second equivalent of phenyl carbamate or phenylurea (and optionally additional catalyst) is added to the reaction mixture, and the temperature is increased to promote coupling and formation of the dicarbamate.

Staged addition promotes a more selective formation of dimer products compared with unstaged addition. Comparative Example 7 (below) shows that when two equivalents of ethyl phenylcarbamate are combined with 0.2 equivalents of trifluoromethanesulfonic acid and one equivalent of methylene bis(ethyl carbamate), and the reaction is performed using the ramped temperature program of the process of the invention, selectivity to dimer products is poorer, and selectivity to polycondensation products ("Other" in Table 1) is higher, compared with the process that uses a staged addition (Examples 1-3).

Also important for high dimer selectivity is the use of a ramped temperature program. During the first stage of the process (in which a first equivalent of an alkyl phenylcarbamate or N,N-dialkyl-N'-phenylurea is added to an equivalent of methylene bis(alkyl carbamate)), it is important to maintain the reaction temperature within the range of about 20° C. to about 55° C. A preferred range is from about 40° C. to about 50° C. If the reaction temperature exceeds about 55° C during this stage, polycondensation reactions become important, and selectivity to dimers diminishes as a consequence (see Comparative Example 9).

During the second stage of the process of the invention (in which a second equivalent of alkyl phenylcarbamate or N,N-dialkyl-N'-phenylurea is added to the intermediate product), it is important to maintain a reaction temperature within the range of about 60° C. to about 100° C. A preferred range is from about 65° C. to about 75° C. If the reaction temperature is not increased in the second stage, reaction of the intermediate product will be incomplete; and selectivity to dimer products will be relatively low (see Comparative Example 8).

The process of the invention is optionally performed in the presence of an organic solvent. Any solvent that is essentially inert to the alkylation conditions can be used. Suitable organic solvents for the process include, for example, aliphatic and aromatic hydrocarbons, halogenated aliphatic and aromatic hydrocarbons, nitro-substituted aliphatic and aromatic hydrocarbons, and the like, and mixtures thereof. Particularly preferred are polar aprotic solvents such as nitromethane, dimethylsulfoxide, acetonitrile, N,N-dimethylformamide, and the like.

The following examples merely illustrate the invention. Those skilled in the art will recognize numerous variations that are within the spirit of the invention and scope of the claims.

EXAMPLES 1-6

Preparation of Diphenylmethane Dicarbamates Staged addition of Ethyl phenylcarbamate w/ Temp. Ramping A 100-mL 3-neck round-bottom flask equipped with magnetic stirring bar, reflux condenser, jacketed addition funnel, and rubber septum is charged with methylene bis(ethyl carbamate) (1.84 g) and nitromethane (5.1 mL). A solution containing ethyl phenylcarbamate (1.49 g), acid catalyst (0.1 eq., see Table 1), and nitromethane (5.0 mL) is charged to the addition funnel.

TABLE I
PREPARATION OF DIPHENYLMETHANE DICARBAMATES

| Ex # | Acid | Stage 1 Temp (°C.) | Stage 1 Time (h) | Stage 2 Temp (°C.) | Stage 2 Time (h) | Conv. (%) | Selectivity (%) Dimers | Interm. | Other |
|---|---|---|---|---|---|---|---|---|---|
| 1 | F$_3$CSO$_3$H | 45 | 2 | 65 | 5 | 78 | 93 | 0 | 7 |
| 2 | F$_3$CSO$_3$H$^a$ | 45 | 2 | 65 | 5 | 81 | 88 | 0 | 12 |
| 3 | F$_3$CSO$_3$H$^{a,b}$ | 45 | 2 | 65 | 5 | 75 | 86 | 0 | 14 |
| 4 | phosphotungstic acid | 45 | 2 | 65 | 5 | 85 | 73 | 19 | 8 |
| 5 | SbCl$_5$ | 45 | 2 | 65 | 5 | 87 | 76 | 9 | 15 |
| 6 | SbCl$_5$/ClSO$_3$H | 45 | 2 | 65 | 5 | 87 | 77 | 7 | 16 |
| C7 | F$_3$CSO$_3$H$^c$ | 45 | 2 | 65 | 5 | 83 | 62 | 13 | 25 |
| C8 | F$_3$CSO$_3$H | 50 | 2 | 50 | 5 | >99 | 57 | 30 | 13 |
| C9 | F$_3$CSO$_3$H | 60 | 2 | 60 | 5 | 82 | 73 | 6 | 21 |

$^a$Methylene bis(methyl carbamate) is used in place of methylene bis(ethyl carbamate)
$^b$Intermediate aryl-alkyl dicarbamate is isolated by filtration after Stage 1, resuspended in solvent, and combined with additional ethyl phenylcarbamate and catalyst as described in the experimental section.
$^c$All reagents are combined initially; not a staged addition of EPC
Products:
Dimers = diphenylmethane dicarbamates (mixture of 2,4'-and 4,4'-isomers)
Interm. = aryl-alkyl dicarbamate intermediate products
Other = uncharacterized mixture of compounds including polycondensation products The ethyl phenylcarbamate/acid solution is added dropwise to the stirred mixture, which is stirred at 45° C. for 2 hours following the addition. An additional equivalent of ethyl phenylcarbamate (1.49 g) and another 0.1 eq. of acid are added in the same manner as before. The reaction mixture is then heated at 65° C. for 5 hours. The observed products are the desired dimers (2,4'- and 4,4'- isomers, mostly 4,4'-), an intermediate product (aryl-alkyl dicarbamate), and other unidentified polymeric condensation products (see Table 1 for % conversion and selectivities).

The general procedure outlined above is modified for Examples 2 and 3 as follows. Examples 2 and 3 are performed using an equivalent amount of methylene bis(methyl carbamate) in place of methylene bis(ethyl carbamate). In Example 3, the intermediate aryl-alkyl dicarbamate is isolated by filtration after the two-hour/45° C. heating stage (90% yield based on ethyl phenylcarbamate; 96% purity by H NMR spectroscopy). The filtered solids are resuspended in nitromethane and are combined with additional ethyl phenylcarbamate and acid as described above.

Comparative Example 7

All reagents combined at 45° C.; Temp. Ramping used

The procedure of Examples 1-6 is followed with these modifications: Ethyl phenylcarbamate (EPC) (3.0 g), methylene bis(ethyl carbamate) (1.84 g), trifluoromethanesulfonic acid (0.2 eq.) and nitromethane (10 mL) are combined and stirred at 45° C. for 2 hours, then at 65° C. for 5 h. Thus, all of the reagents are combined initially (no staged addition of ethyl phenylcarbamate). The temperature program followed is identical to that used in Examples 1-6. Results appear in Table 1. Selectivity to dimer products drops to 62%, while selectivity to condensation products increases to 25%. This example illustrates the importance of a staged addition of EFC in giving high dimer selectivity.

COMPARATIVE EXAMPLE 8

Staged Addition of EPC/Acid; Temp Maintained at 50° C.

The procedure of Examples 1-6 is followed except that the temperature is kept at 50° C. throughout the course of the experiment. Thus, the reaction mixture is stirred for 2 h at 50° C. following addition of the first equivalent of ethyl phenylcarbamate, and is kept at 50° C. for 5 hours following addition of the second equivalent of EPC. Results appear in Table 1. Selectivity to dimer products is 57%, and 30% of the product is the aryl-alkyl dicarbamate intermediate. This example highlights the importance of increasing the reaction temperature during the second stage of the process to promote conversion of the intermediate product to the desired dimer products.

COMPARATIVE EXAMPLE 9

Staged Addition of EPC/Acid; Temp Maintained at 60° C.

The procedure of Examples 1-6 is followed except that the temperature is kept at 60° C. throughout the course of the experiment. Results appear in Table 1. Selectivity to dimer products is good (73%), but a substantial amount of condensation products (21%) are obtained. This example shows that a relatively low (20°-55° C.) temperature is needed for the first stage to minimize the formation of unwanted condensation products.

We claim:

1. A selective process for making a diphenylmethane bis(dialkylurea), said process comprising:
   (a) slowly adding a mixture of an N,N-dialkyl-N'-phenylurea and an effective amount of an acid to a methylene bis(alkyl carbamate) at a temperature within the range of about 20° C. to about 55° C. to produce an aryl urea-alky carbamate; and
   (b) heating the aryl urea-alkyl carbamate in the presence of additional N,N-dialky-N'-phenylurea at a temperature within the range of about 60° C. to about 100° C. for a time sufficient to produce the diphenylmethane bis(dialkylurea).

2. The process of claim 1 wherein the acid is a protic acid that has a $pK_a$ less than about 0.

3. The process of claim 1 wherein the methylene bis(alkyl carbamate) is selected from the group consisting of methylene bis (methyl carbamate) and methylene bis(ethyl carbamate).

4. The process of claim 1 wherein the molar ratio of N,N-dialkyl-N'-phenylurea to methylene bis(alkyl carbamate) in step (a) is within the range of about 0.8 to about 1.5.

5. The process of claim 1 wherein the amount of acid used is maintained within the range of about 0.05 to about 0.15 equivalents per equivalent of N,N-dialkyl-N'-phenylurea.

6. The process of claim 1 wherein the acid is a protic acid is selected from the group consisting of trifluoromethanesulfonic acid, phosphotungstic acid, antimony pentachloride/chlorosulfonic acid, fluorosulfonic acid, trifluoroacetic acid, fluoroboric acid, hydrochloric acid, and sulfuric acid.

7. The process of claim 1 wherein the process is performed in the presence of an organic solvent.

8. The process of claim 1 wherein a methylene bis(dialkylurea) is used in place of the methylene bis(alkylcarbamate).

* * * * *